(12) United States Patent
Michelle (10) Patent No.: US 6,520,922 B2
(45) Date of Patent: Feb. 18, 2003

(54) DEVICES FOR COLLECTING ANIMAL SEMEN AND METHOD OF USE

(75) Inventor: Beth Michelle, Acton, CA (US)

(73) Assignee: Double H.Ranch Products, LLC, Acton, CA (US)

( * ) Notice: Subject to any disclaimer, the term of this patent is extended or adjusted under 35 U.S.C. 154(b) by 0 days.

(21) Appl. No.: 09/804,122

(22) Filed: Mar. 13, 2001

(65) Prior Publication Data

US 2002/0133090 A1 Sep. 19, 2002

(51) Int. Cl.[7] ............................................... A61B 10/00
(52) U.S. Cl. ......................................... 600/562; 600/35
(58) Field of Search ............................... 600/33, 35, 38, 600/562, 573, 582; 128/830, 834, 835, 837, 839–842, 844; 604/317, 327, 328, 330, 331, 338–341, 345–347, 349–353; 119/174, 854

(56) References Cited

U.S. PATENT DOCUMENTS

| 899,251 | A | * | 9/1908 | Graham | 604/330 |
| 4,320,752 | A | * | 3/1982 | Comparetto | 128/844 |
| 4,690,678 | A | * | 9/1987 | Douglas-Hamilton | 604/349 |
| 4,972,849 | A | | 11/1990 | Park et al. | |
| 5,005,589 | A | | 4/1991 | Hwang | |
| 5,111,831 | A | * | 5/1992 | Foggia | 128/842 |
| 5,419,341 | A | | 5/1995 | Galasso | |
| 5,515,862 | A | | 5/1996 | Artsi et al. | |
| 5,598,852 | A | | 2/1997 | Spery | |
| 5,685,871 | A | * | 11/1997 | Lindholm-Ventola | 604/349 |
| 5,715,839 | A | | 2/1998 | Strauss et al. | |
| 6,135,112 | A | * | 10/2000 | Harrison et al. | 128/844 |
| 6,250,303 | B1 | * | 6/2001 | Delaney | 128/844 |
| 6,321,751 | B1 | * | 11/2001 | Strauss et al. | 128/844 |

* cited by examiner

Primary Examiner—Eric F. Winakur
Assistant Examiner—Charles Marmor, II
(74) Attorney, Agent, or Firm—William W. Haefliger (57) ABSTRACT

A device for collecting animal semen for later artificial insemination.

14 Claims, 7 Drawing Sheets

DEVICES FOR COLLECTING ANIMAL SEMEN AND METHOD OF USE

BACKGROUND OF THE INVENTION

The present invention pertains generally to artificial insemination in animals, and in particular to both female and male condom-like devices which serve to collect semen for that purpose.

Animal breeding is a large industry throughout the world. Particularly in the field of horse breeding, prized stallions can be worth $100,000 to $20,000,000 with stud fees ranging from $10,000 to $150,000. In view of the sizable financial investment represented by the animals, it is most desirable to provide the maximum probability of breeding success with the minimum possibility of injury to the breeding animals. In each breeding encounter, there is always risk of injury to a breeding pair of animals, such as through kicks or falls. In some instances the injury can be so severe that one or both of the animals has to be destroyed. For example, some mares kick during breeding. If the mare kicks the leg of the stallion, the leg may break thereby necessitating destruction of the stallion. Therefore to minimize this risk, artificial insemination is usually employed wherein a large amount of semen bearing sperm is collected from one breeding encounter and then utilized to impregnate several mares. This technique is also useful since the breeding animals do not have to be physically brought together, but can rather reside great distances apart.

A problem exists however with the method of collecting the sperm. The current method uses a leather "boot" costing about $500. The stallion is brought to a mare that is in heat, thereby by precipitating sexual arousal. Under the guidance of one or more handlers, the stallion mounts the mare. Rather than allowing the stallion's penis to enter the mare's vagina, a handler manually deflects the penis into the boot, thereby hoping to fool the stallion into believing that a natural sexual position has been attained. Unfortunately, in many instances upon feeling the unnatural boot, the stallion becomes angry, and commences to scream, dismounts the mare and proceeds to kick and stomp. Obviously, such behavior represents a potential danger to horses and handlers alike.

The present invention overcomes the aforementioned difficulties by utilizing specially designed condom-like devices which (1) allow the breeding process to take place in a natural way thereby reducing the risk of injury to the participants, and (2) which ensures that a maximum amount of semen is collected.

Condoms for humans are well known in the art. These devices are utilized (1) to prevent disease, and (2) as a contraceptive. For example, in the area of female condoms, U.S. Pat. No. 5,512,862 illustrates a condom for use by a female user. The condom has a flexible tube for insertion into the vagina, the tube having a sealed end and an open end, a shield sealingly attached to or integrally formed with the open end. An adhesive is applied to the external portion of the shield for detachably attaching the condom to the female user. The condom includes a plurality of semi-ridged rings which serve to prevent it from collapsing radially. U.S. Pat. No. 5,598,852 shows a receptive condom assembly to be received by a passive sexual organ. The condom has a cushioning ring affixed to the open end which always resides outside of the passive sexual organ. The cushioning ring limits the depth of insertion in the passive sexual organ. An insertion element is utilized to install the condom in the passive sexual organ.

In the area of male condoms, U.S. Pat. No. 4,972,849 discloses a condom (sanitary contraception device) which is provided with a cap. The cap is integrally attached into an arcuate top portion of the main portion of the condom. The cap covers almost the whole area of the head portion of a male sexual organ in order to protect the head portion from being subjected to sensitizations and stimulation. U.S. Pat. No. 5,005,589 consists of a condom having a body, a sperm cell extending forward from the body, and a vertical narrow flat neck between the body and the cell for the sperm to pass through into the cell. Sperm thus entering the sperm cell will stay in the sperm cell and not flow back into the body. A circumferential recess is included which surrounds the recessed edge under the glans of the penis. U.S. Pat. No. 5,419,341 describes a complementary product for a condom having a closure flap. The closure flap is secured to a flange to cover the open end of a used condom to prevent semen from leaking out of the condom. U.S. Pat. No. 5,715,839 portrays a condom having multiple spaced rings which protect against leakage and spillage.

SUMMARY OF THE INVENTION

It is a major object of the invention to provide method and apparatus to overcome problems and difficulties associated with prior techniques and devices. Basically, the preferred device of the invention includes a flexible sheath having an open end, and opposite closed end, and a mid-portion therebetween; a vulva ring at said open end; and an inner vaginal ring fixedly disposed along that mid-portion. A reservoir or reservoir zone is typically provided at the closed end, to collect and protect the semen, as will be clear. In addition, the reservoir or reservoir zone may include a protuberance to allow cutting of a reservoir tip for semen removal, that zone being separate from the main interior and elongated compartment of the device.

In addition the animal vagina and the vulva may define first and second diameters respectively, the second larger than the first; and the inner vaginal ring may have a third diameter larger than the first diameter but smaller than the second diameter, for purposes as will appear. Also, the sheath mid-portion between the vulva ring and inner vaginal ring may define a fourth diameter which is smaller than the third diameter; and a collar may be provided as will appear.

Another object is to provide a device for collecting animal semen, said device shaped and dimensioned to fit over the penis of a male animal, said device comprising:
 a) a sheath having an open end, an opposite closed end, and a mid-portion therebetween,
 b) said closed end including a separate protective reservoir zone for collecting the semen, and
 c) a valve disposed between said mid-portion and said reservoir zone.

It is a further object to provide methods of use of the improved devices, as referred to.

These and other objects and advantages of the invention, as well as the details of an illustrative embodiment, will be more fully understood from the following specification and drawings, in which:

DRAWING DESCRIPTION

FIG. 4 is a rotated end elevation view of a modified version of the device of FIG. 3;

FIG. 7 is a perspective view of a universal closed end for the device. FIGS. 7 and 8 can apply to either the female or male device;

DETAILED DESCRIPTION

The present invention is directed to devices for collecting animal semen for the purpose of subsequently performing artificial insemination. Two preferred such devices are disclosed, either one of which can be utilized to collect the semen. One device is a condom-like sheath which is inserted into the vagina of a female animal prior to the act of breeding. And, the other device is a condom-like sheath which is placed over the penis of a male animal. In both cases, the devices permit a more natural feeling breeding encounter, wherein there is less danger of the animals becoming distracted, angry, and unruly. Both devices are easy to install and remove, and contain a special reservoir to hold and protect the semen with no chance leaking or spilling. The devices are sanitized and only used once, therefore minimizing any possibility of infection. The present invention is focused upon use with horses or other members of the equine species, however it may be readily appreciated that the principles of the present invention may be practiced upon other animal species as well. These include domestic, wild and exotic animals. The following paragraphs discuss the structure and features of both the female and male devices.

Female Device

Figure 1:
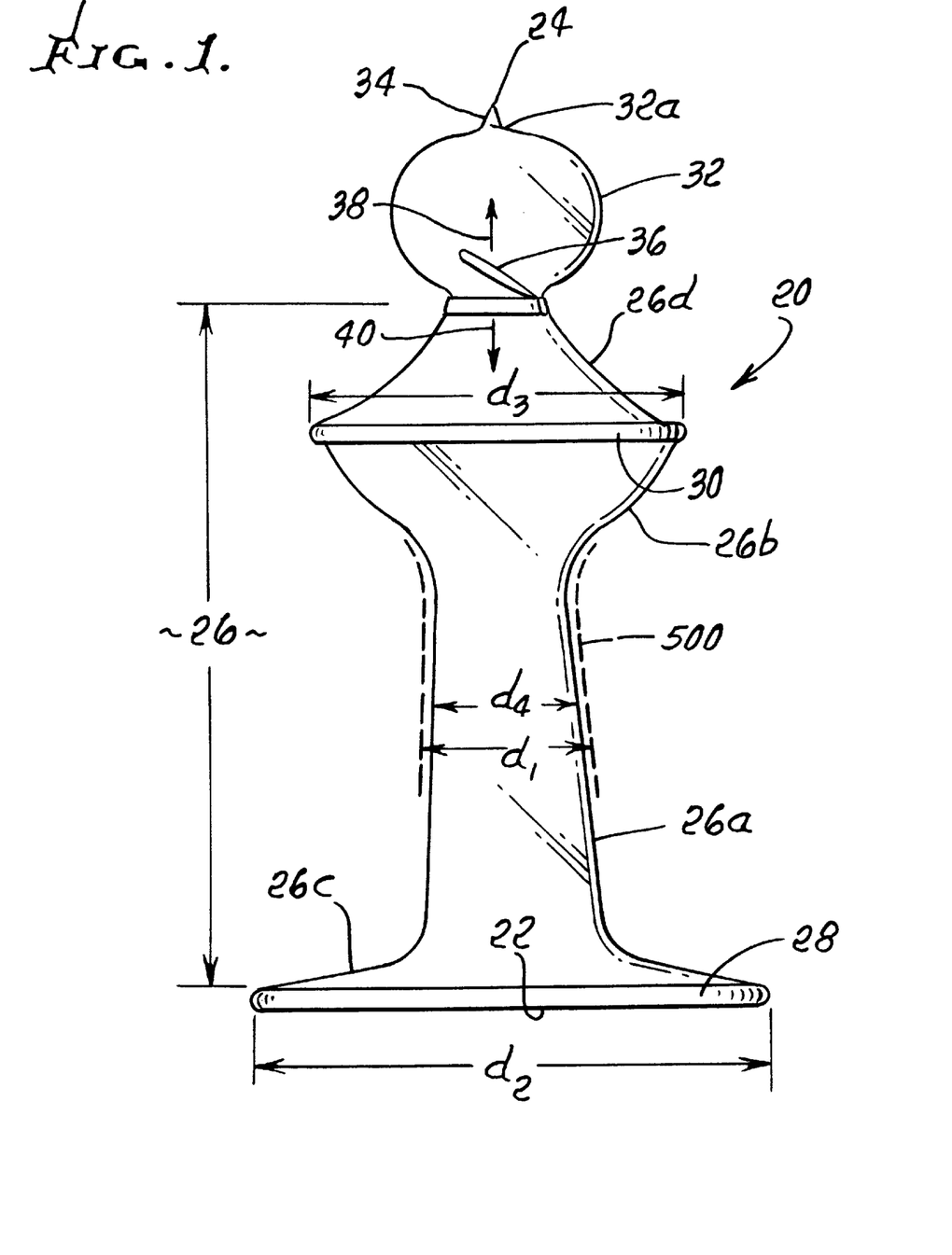
FIG. 1 is a side elevation of a device for collecting animal semen in accordance with the present invention. The devices of FIGS. 1–4 are shaped and dimensioned to be installed in the vagina of a female animal.

Referring initially to FIG. 1, there is illustrated at 20 a side elevation view of a device for collecting animal semen in accordance with the present invention. Device 20 is shaped and dimensioned to fit into the vagina 500 of a female animal, and comprises a sheath comprised of thin membrane such as latex having an open end 22, an opposite closed end 24, and a mid-portion 26 therebetween. Open end 22 includes a vulva ring 28 projecting radially outwardly as in the form of a flange, from reduced diameter tubular portion 26a of 26. An inner vaginal ring 30 is fixedly disposed along mid-portion 26, and when installed, holds device 20 in a position just before the cervix. Ring 30 is of greater diameter than sheath portion 26a, which flares at 26b to meet 30. In contrast to human female condoms, inner vaginal ring 30 is fixed (as by molding) to mid-portion 26. This allows device 20 to be more rapidly positioned within the vagina 500. The vulva ring 28 and inner vaginal ring 30 are sized to be larger than the vaginal canal 500 of the female animal. Therefore, once installed, these rings hold device 20 in place within the animal's vagina 500. That is, vulva ring 28 prevents device 20 from being forced (by the male's penis) completely into the vagina 500, and inner vaginal ring 30 prevents device 20 from unwantingly exiting the vagina 500.

In terms of dimensions, the vagina 500 of the female animal has a first diameter d1. Vulva ring 28 has a second diameter d2 which is larger than d1. Inner vaginal ring 30 has a third diameter d3 which is greater than first diameter d1, and less than second diameter d2. The mid-portion 26a between the vulva ring 28 and the inner vaginal ring 30 has a fourth diameter d4 between flares 26b and 26c which is less than the third diameter d3 of the inner vaginal ring 30. Typically mid-portion 26a between vulva ring 28 and inner vaginal ring 30 has a generally hourglass shape. It will be noted that the enlarged diameter in the area of inner vaginal ring 30 also conveniently accommodates the swelling or "flowering" of the head of the male animal's penis, which occurs after ejaculation.

Closed end 24 includes a protective reservoir zone or tip 32 for collecting and containing the semen. In the shown embodiment, reservoir tip 32 has a bulbous "balloon" shape which both accommodates a large quantity of semen, and lessens the chance that the reservoir tip 32 will fold back or invert during either the installation or breeding process. Thus, tip 32 acts protectively, and is spaced from 30 by reducing flare 26d. Reservoir tip 32 may include a protuberance 34 to allow convenient cutting or clipping of the tip to remove the captured semen via an exit port 32a. Zone or tip 32 extends forwardly of the main elongated extent of the device.

A one-way flap valve 36 is disposed along mid-portion extent 26d between inner vaginal ring 30 and reservoir tip 32. Under ejaculatory pressure, the semen is forced past one-way valve 36 and into reservoir tip 32 in direction 38. One-way valve 36 is resiliently biased in direction 40 to a closed position at seat 36a thereby trapping the semen in the interior of reservoir tip 32 after ejaculation. In a preferred embodiment, the inside of device 20 is lubricated as by an oil to permit ease of movement. The lubricating substance is neutral and does not affect the semen and sperm.

Figure 2:
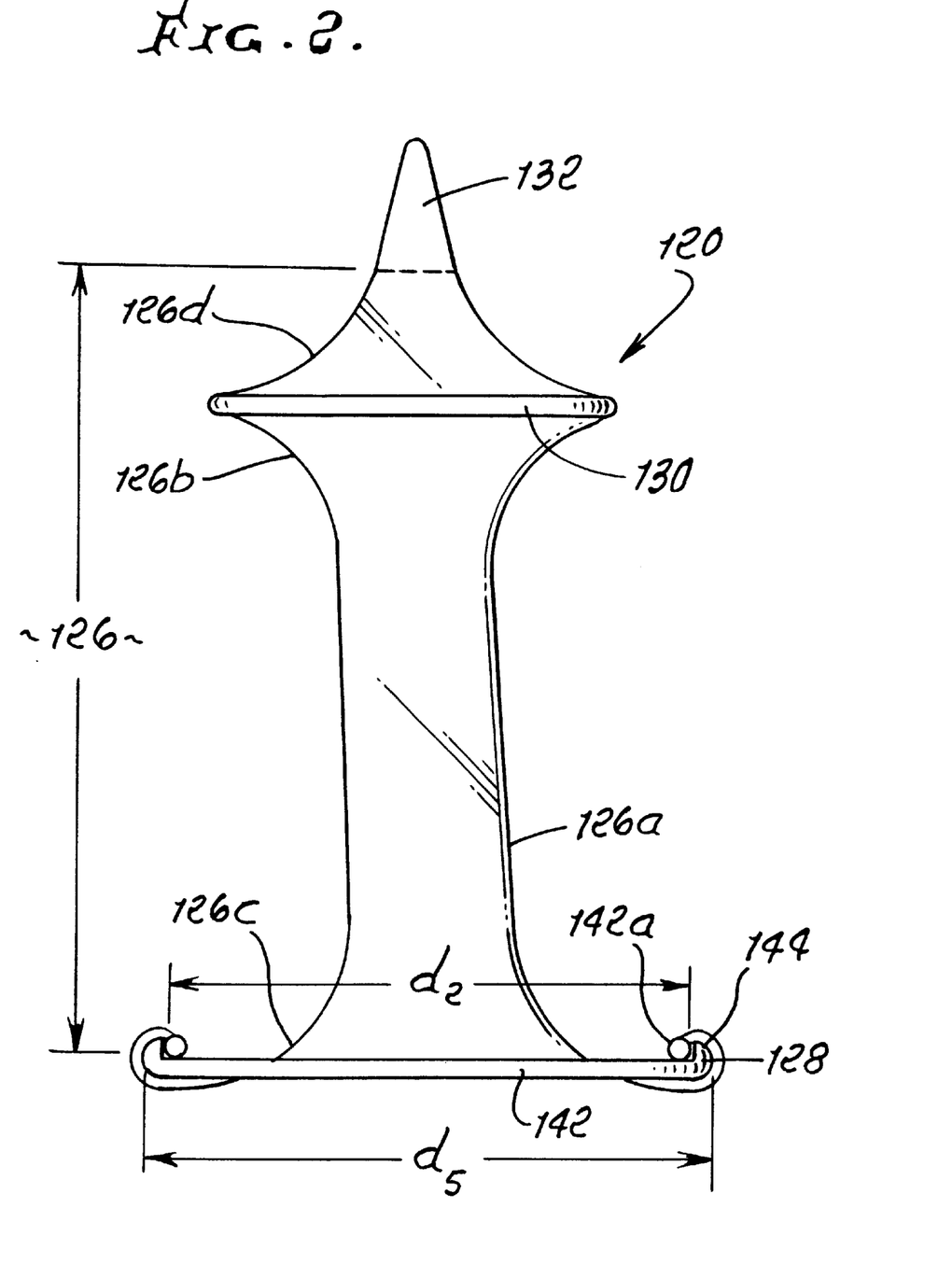
FIG. 2 is a side elevation view of a second embodiment.
Figure 3:
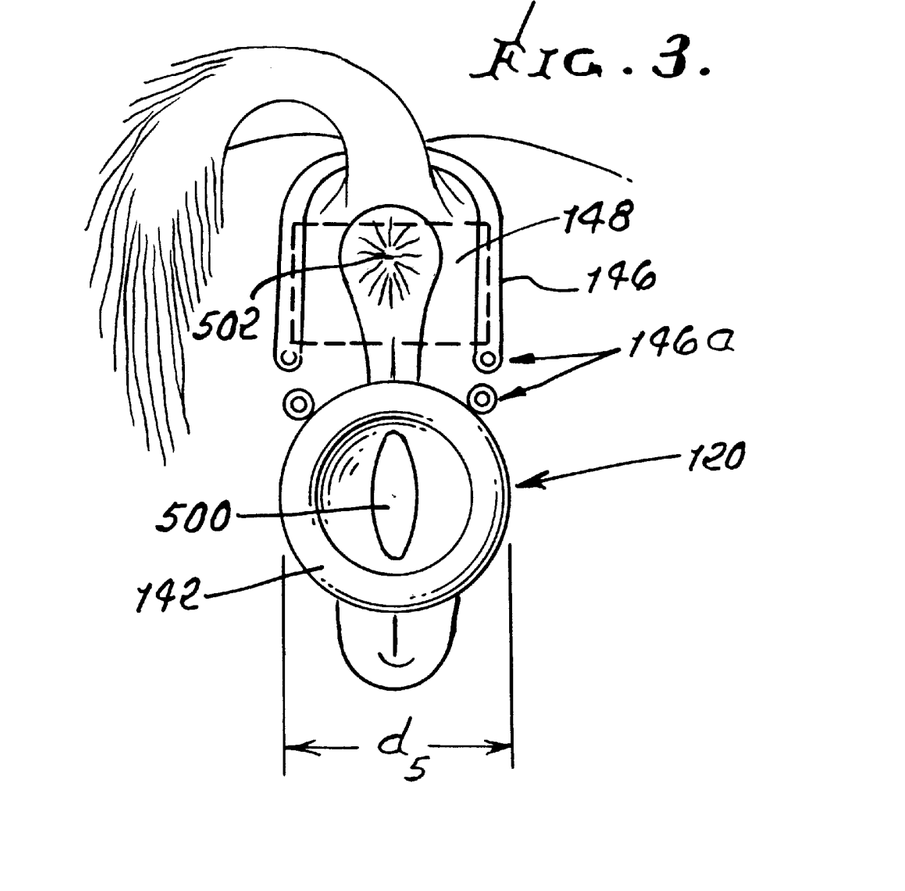
FIG. 3 is an end elevation view of the device of FIG. 2 installed in the vagina of an animal.

FIG. 2 is a side elevation view of a second embodiment of the female device, generally designated as 120, and FIG. 3 is an end elevation view of device 120 installed in the vagina 500 of a female animal. Device 120 includes mid-portion 126, vulva ring 128, inner vaginal ring 130, and tapering reservoir tip 132. See also mid-portion extents 126a, 126b, 126c, and 126d generally and respectively corresponding to extents 26a, 26b, 26c, and 26d in FIG. 1. This embodiment does not include a one-way valve, but does include a separate, substantially circular, washer-shaped collar 142 having a fifth diameter d5 which is slightly larger than diameter d2 of the vulva ring 128 upon which collar 142 fits as by clipping at 142a. In a preferred embodiment, device 120 is made of an elastic material such as latex rubber, and therefore vulva ring 128 may be stretched to circumferentially engage (hook around) a lip 144 on washer-shaped collar 142. When thus installed, washer-shaped collar 142 prevents device 120 from being pushed into the animal's vagina 500 by the thrusting of the male animal's penis.

FIG. 3 also illustrates a tail strap 146 which is selectively connectable by buttons or snaps 146a or other means to washer-shaped collar 142. Tail strap 146 also serves to prevent device 120 from being pushed into the animal's vagina 500. In another embodiment, an anus cover 148 is selectively connectable to tail strap 146. Anus cover 148 prevents the penis from inadvertently entering the anus 502 of the female animal.

FIG. 4 is a rotated end elevation view of a modified version of device 120. In this embodiment, collar 142 is oval rather than substantially circular. The oval shape provides added protection against device 120 being forced into the vagina 500 of the animal.

Devices 20 and 120 may be easily and rapidly installed in the vagina 500 of the female animal. The erect penis of the male animal is then guided into the device 20 or 120. After ejaculation, the penis is removed from the device. The device 20 or 120 is then removed from the female animal, and the semen is removed and appropriately stored. In a preferred embodiment, the semen is removed by making a cut in the device, as at 24, as described.

Male Device

Figure 5:
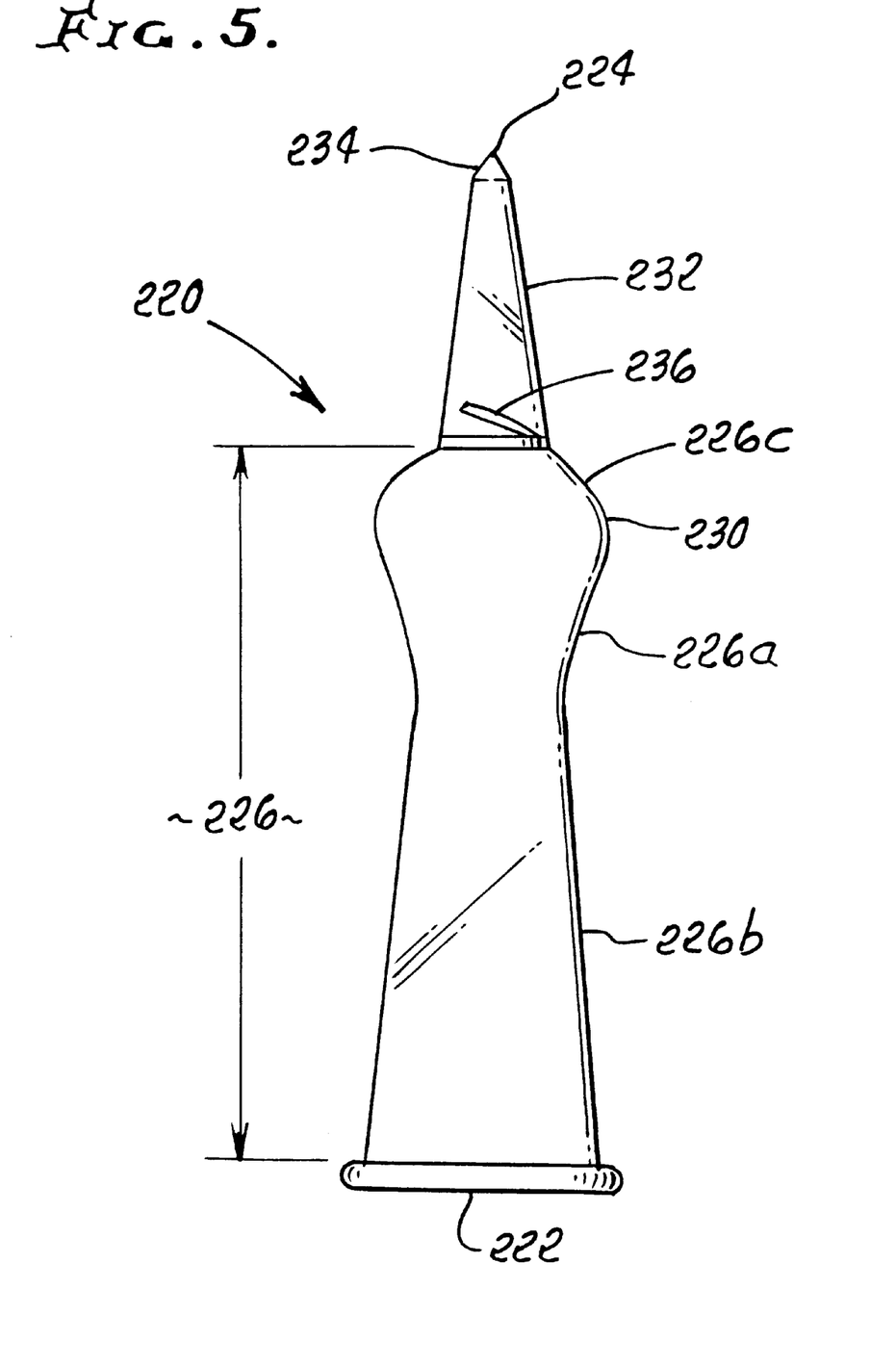
FIG. 5 is a side elevation view of a device for collection animal semen in accordance with the present invention. The device of FIGS. 5 and 6 is shaped and dimensioned to be installed over the penis of a male animal.

Referring now to FIG. 5 there is illustrated a side elevation view of a sheath device 220 for collecting animal semen in accordance with the present invention. Device 220 is shaped and dimensioned to fit over the penis 504 (refer to FIG. 6) of a male animal, and comprises a thin membraned sheath having an open end 222, an opposite closed end 224, and an elongated mid-portion 226 therebetween. Closed end 224 includes a reservoir tip or zone 232 for collecting and containing semen, and a one-way valve 236 disposed between mid-portion 226 and reservoir tip 232. Reservoir tip 232 can either be tapered as shown, or can have a bulbous "balloon" shape (refer also to FIG. 7). Also, reservoir tip 232 includes an endwise protuberance 234 to allow convenient cutting or clipping of reservoir tip 232 to remove the captured semen via an end port. Mid-portion 226 includes an enlarged portion 230 which accommodates the swelling or "flowering" of the head of the male animal's penis, which occurs after ejaculation. Mid-portion 226 tapers at 226a, 226b, and 226c, as shown.

Figure 6:
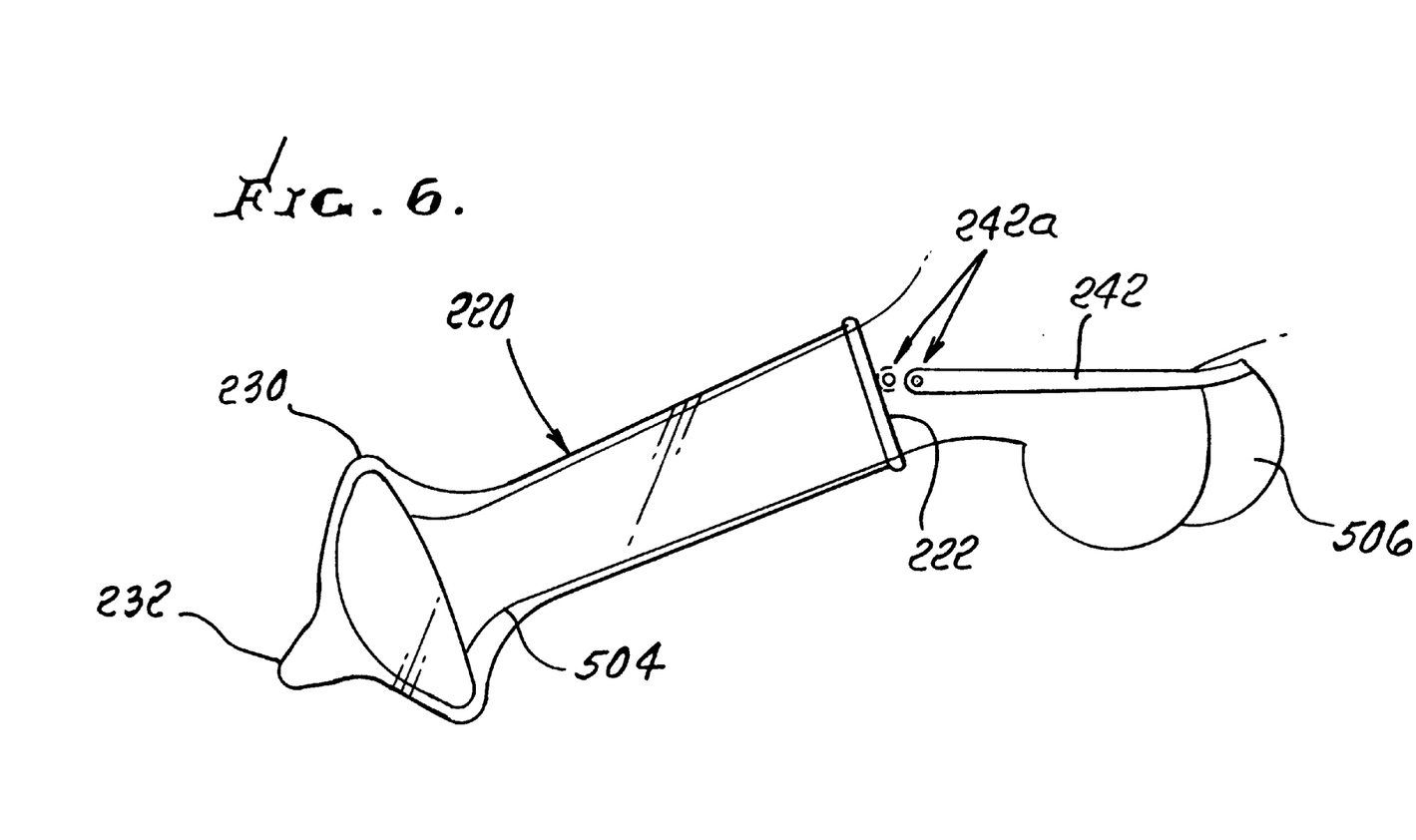
FIG. 6 is a side elevation view of a second embodiment.

FIG. 6 is a side elevation view of a second embodiment of device 220 showing the penis 504 of the male animal inserted therein. A scrotum strap 242 is selectively connectable via snaps 242a to sheath open end 222. Scrotum strap 242 surrounds the scrotum 506 of the animal 500 and holds device 220 on the penis of the animal 500. Scrotum strap 242 may be attached to device 220 by any convenient means, such as by buttons or snaps.

Figure 7:
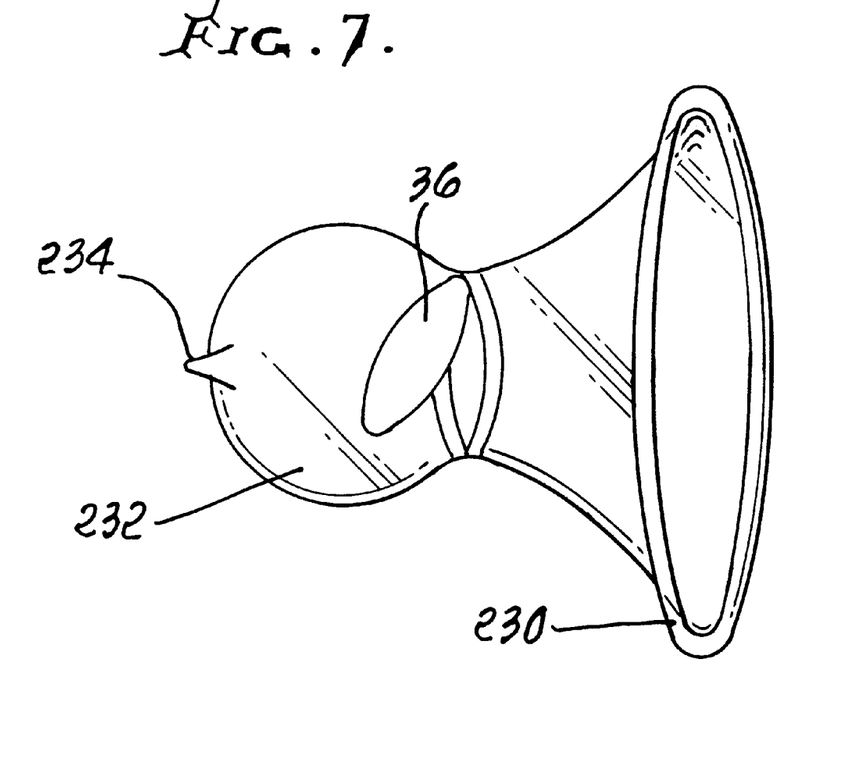
Figure 8:
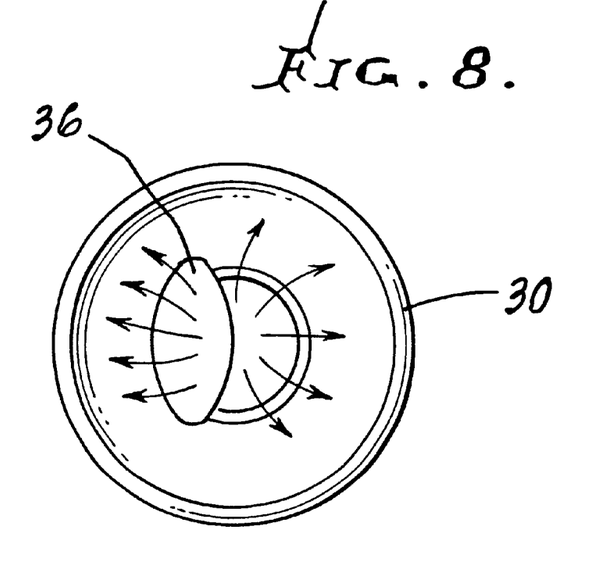
FIG. 8 is a top plan view of the device of FIG. 7.

FIGS. 7 and 8 are perspective and top plan views respectively of a universal end which may be used with female devices 20 and 120, or with male device 220. The universal end has an enlarged area 230, a reservoir 232, a protuberance 234, and a one-way valve 36, as previously referred to.

Figures 9, 10, 11:
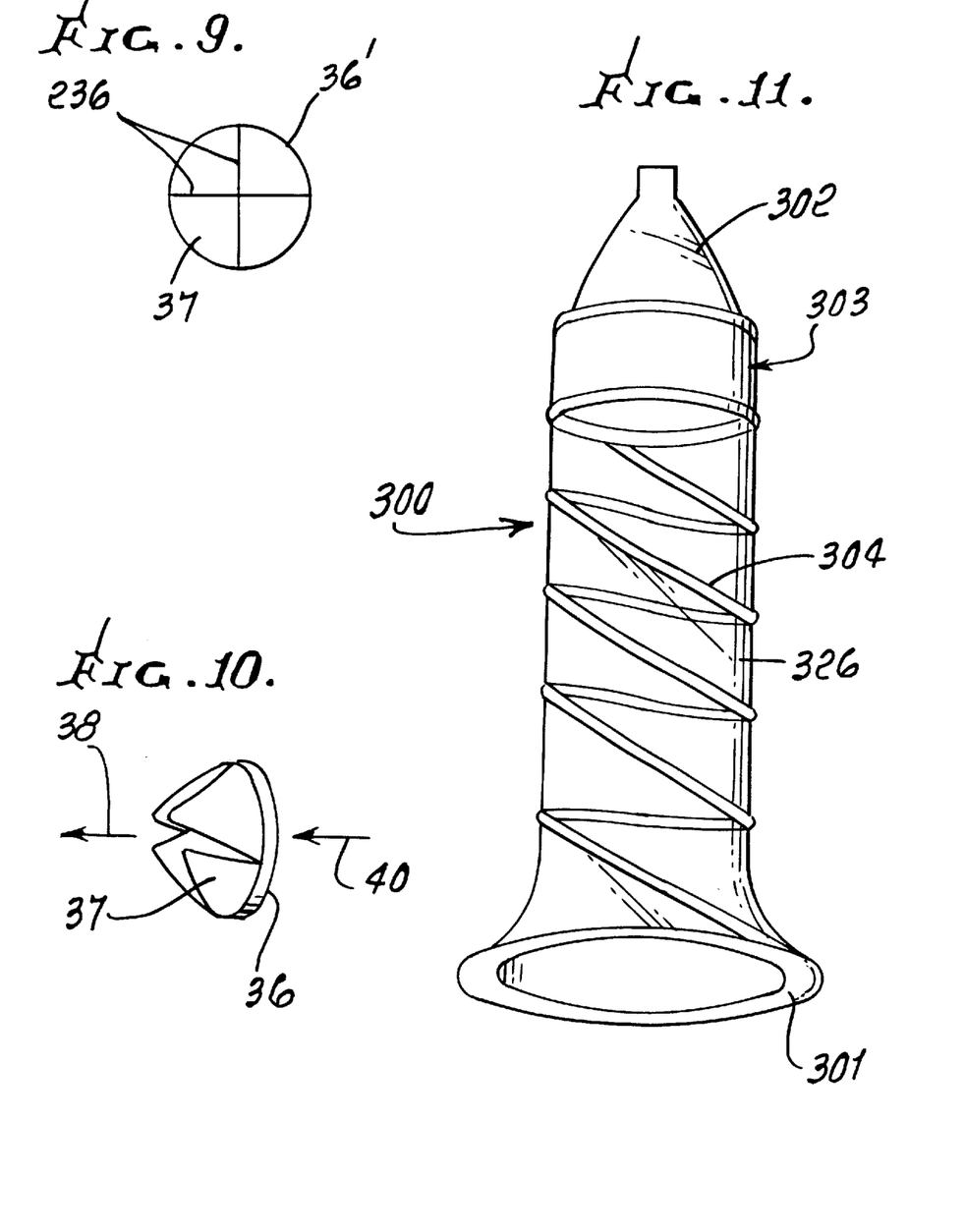
FIG. 9 is a top plan view of a second one-way valve embodiment.
FIG. 10 is a perspective view of the second one-way valve embodiment.
FIG. 11 is a view like FIG. 1 showing a further modification.

FIGS. 9 and 10 are top plan and perspective views respectively, of a second one-way valve embodiment. In this embodiment, one-way valve 36' comprises a substantially circular aperture having a plurality of intersecting slits 236 which define a plurality of teeth 37. Under ejaculatory pressure, the semen is forced in direction 38 past teeth 37 and into reservoir tip 32. Teeth 37 are resiliently biased in direction 40 to a closed position, thereby trapping the semen in reservoir tip 32.

Device 220 may be easily and rapidly installed on the penis 504 of the male animal. The erect penis of the male animal is then guided into the vagina 500 of the female animal. After ejaculation, the penis 504 is removed from the female's vagina 500. The device is then removed from the penis 504, and the semen is removed and appropriately stored. In a preferred embodiment, the semen is removed by making a cut in the device.

In a preferred embodiment, devices 20, 120, and 220 are fabricated of latex rubber, however numerous thin membrane-type materials could also be used, such as other polymers. Also, it may be readily appreciated that devices 20, 120, and 220 can be fabricated in a variety of sizes in order to accommodate animals of different sizes.

FIG. 11 shows a modified device 300 to fit a female. Ring 301 corresponds to ring 28 of FIG. 1; tip or reservoir 302 corresponds to tip 32; and annular band 303 corresponds to ring 30. A spiral protuberance 304 extends along and about mid-region 326, to engage the vaginal wall and retain the device 300 in position during use, as described.

The preferred embodiments of the invention described herein are exemplary and numerous modifications, dimensional variations, and rearrangements can be readily envisioned to achieve an equivalent result, all of which are intended to be embraced within the scope of the appended claims.

I claim:

1. A method of collecting animal semen, comprising the steps of:
   a) providing a device for collecting animal semen, said device being shaped and dimensioned to fit over the penis of a male animal, said device comprising
      a sheath having an open end, an opposite closed end, and a mid-portion therebetween;
      said closed end including a separate protective reservoir zone for collecting the semen; and
      a valve disposed between said mid-portion and said reservoir zone;
   b) providing a female animal having a vagina;
   c) providing a male animal having a penis;
   d) installing said device on the penis of the male animal;
   e) ensuring that the penis of the male animal is inserted into the vagina of the female animal and positioned for semen collection in said reservoir zone;
   f) after ejaculation, ensuring that the penis of the male animal is removed from the vagina of the female animal;
   g) removing said device from the penis of the male animal; and
   h) removing the semen from said reservoir zone.

2. The method of claim 1, wherein said step of removing the semen from the device further including cutting the device for semen removal.

3. The method of claim 1 wherein said reservoir zone has a bulbous shape.

4. The method of claim 1 wherein said device further includes
   a vulva ring at said open end,
   and an inner vaginal ring fixedly disposed along said sheath mid-portion.

5. The method of claim 4 wherein said device further includes projections on the sheath disposed along said mid-portion between said inner vaginal ring and said reservoir zone.

6. The method of claim 5 wherein said reservoir zone includes a protuberance to allow for cutting of a tip of the reservoir zone, said sheath defining a main inner elongated compartment, said reservoir zone being separate from said compartment.

7. The method of claim 6 wherein said protuberance extends in a spiral, and between said rings.

8. The method of claim 4 wherein said device is adapted to accommodate to the vagina of the female animal having a first diameter, said vulva ring having a second diameter, said second diameter being larger than the first diameter of the female animal; and said inner vaginal ring having a third diameter, said third diameter being greater than the first diameter of the female animal, and said third diameter being less than said second diameter.

9. The method of claim 8 wherein said mid-portion between said vulva ring and said inner vaginal ring defines fourth diameters, said fourth diameters being less than said third diameter, said fourth diameters defining a flare toward the vaginal ring and a flare toward the vulva ring.

10. The method of claim 8 wherein said device further includes a collar having an outer fifth diameter being larger than said second diameter of said vulva ring; and said collar sized to stretchably engage said vulva ring.

11. The method of claim 10 wherein said device further includes a tail strap connected to said collar.

12. The method of claim 11 wherein said device further includes an anus cover connected to said tail strap.

13. The method of claim 8 wherein said collar is one of the following:

i) substantially circular, or ii) substantially oval.

14. A method of collecting animal semen, comprising the steps of:

a) providing a device for collecting animal semen, said device being shaped and dimensioned to fit into the vagina of a female animal, said device comprising a flexible sheath having an open end, an opposite closed end, and a mid-portion therebetween;

a vulva ring at said open end; and an inner vaginal ring fixedly disposed along said mid-portion;

b) providing a female animal having a vagina;

c) providing a male animal having a penis;

d) installing said device in the vagina of the female animal;

e) ensuring that the penis of the male animal is inserted into said device and positioned for semen collection, f) after ejaculation, ensuring that the penis of the male animal is removed from said device, g) removing said device from the female animal, and h) removing the semen from the device, wherein said step of removing the semen from the device further includes collecting semen in a forward separate reservoir in the device, for protection, and cutting the device.

* * * * *